(12) United States Patent
Dinsmore

(10) Patent No.: US 10,477,661 B2
(45) Date of Patent: Nov. 12, 2019

(54) CYLINDRICAL HIGH VOLTAGE ARRANGEMENT FOR A MINIATURE X-RAY SYSTEM

(71) Applicant: THERMO SCIENTIFIC PORTABLE ANALYTICAL INSTRUMENTS INC., Tewksbury, MA (US)

(72) Inventor: Mark T. Dinsmore, Colorado Springs, CO (US)

(73) Assignee: THERMO SCIENTIFIC PORTABLE ANALYTICAL INSTRUMENTS INC., Tewksbury, MA (US)

( * ) Notice: Subject to any disclaimer, the term of this patent is extended or adjusted under 35 U.S.C. 154(b) by 206 days.

(21) Appl. No.: 15/651,485

(22) Filed: Jul. 17, 2017

(65) Prior Publication Data

US 2018/0054879 A1  Feb. 22, 2018

Related U.S. Application Data

(60) Provisional application No. 62/376,020, filed on Aug. 17, 2016.

(51) Int. Cl.
| | |
|---|---|
| H05G 1/10 | (2006.01) |
| H05G 1/02 | (2006.01) |
| G01N 23/223 | (2006.01) |
| H02M 7/10 | (2006.01) |
| H05G 1/12 | (2006.01) |
| H05G 1/06 | (2006.01) |

(52) U.S. Cl.
CPC .............. *H05G 1/10* (2013.01); *H02M 7/106* (2013.01); *H05G 1/02* (2013.01); *H05G 1/06* (2013.01); *H05G 1/12* (2013.01); *G01N 23/223* (2013.01); *G01N 2223/301* (2013.01)

(58) Field of Classification Search
CPC .. H05G 1/10; H05G 1/08; H05G 1/06; H05G 1/12; H05G 1/025; G01N 23/223; G01N 2223/301
See application file for complete search history.

(56) References Cited

U.S. PATENT DOCUMENTS

| | | | | |
|---|---|---|---|---|
| 2,430,904 | A | * 11/1947 | Boldingh | ............ A01M 7/0092 257/42 |
| 7,657,003 | B2 | 2/2010 | Adams | |
| 9,281,156 | B2 | 3/2016 | Dinsmore | |
| 2014/0294156 | A1* | 10/2014 | Wang | ........................ H05G 1/12 378/109 |

FOREIGN PATENT DOCUMENTS

| | | |
|---|---|---|
| CN | 2083391 U | 8/1991 |
| CN | 101040355 A | 9/2007 |
| CN | 101048028 A | 10/2007 |
| CN | 104335468 A | 2/2015 |
| CN | 105144335 A | 12/2015 |

OTHER PUBLICATIONS

First Office action dated Mar. 12, 2019, to CN Patent Application No. 201710702025.X.

* cited by examiner

*Primary Examiner* — David P Porta
*Assistant Examiner* — Fani Boosalis
(74) *Attorney, Agent, or Firm* — William R McCarthy, III

(57) ABSTRACT

An embodiment of a device for producing x-rays is described that comprises an x-ray tube and a high-voltage power supply electrically coupled to the x-ray tube, where the high-voltage power supply comprises a first stack of D shaped capacitors arranged in an opposed relationship with a second stack of D shaped capacitors.

17 Claims, 4 Drawing Sheets

CYLINDRICAL HIGH VOLTAGE ARRANGEMENT FOR A MINIATURE X-RAY SYSTEM

CROSS-REFERENCE TO RELATED APPLICATION

This application claims the benefit of U.S. provisional patent application No. 62/376,020, filed Aug. 17, 2016. The contents of this application are incorporated by reference in their entirety

BACKGROUND OF THE INVENTION

Field of the Invention

The invention relates to an x-ray system characterized by having a reduced size such as are found in portable/handheld devices, and in particular, to techniques for manufacturing and using the x-ray system.

Description of the Related Art

There is an interest in compact, low power consumption x-ray devices for a variety of purposes, including portable x-ray analytical instruments capable of providing highly accurate detection capabilities. Providing small form x-ray devices such as portable x-ray fluorescence (XRF) instruments has, however, been a challenge.

For example, the size of conventional high voltage power supplies necessary to power x-ray equipment has constrained designers. This has been exacerbated by associated electrical insulation requirements. x-ray tubes typically used in portable instruments require up to 60,000 Volts accelerating voltage and <1 mA of beam current. The most beneficial arrangement for portable x-ray instrumentation is a grounded anode x-ray source such that a negative high voltage is applied to a cathode end of the x-ray tube, while the output anode end is held at ground potential and presented to the sample. Operation for these types of portable XRF instruments requires independent control of the accelerating voltage and the beam current.

Miniature x-ray tubes with a grounded anode design typically require up to 1 watt of low voltage power applied to a thermionic type filament in order to heat the filament sufficiently to emit electrons. The difficulty is that a relatively high power source is necessary and positioned in close proximity to the x-ray tube which needs to be isolated from ground potential by the full high voltage being applied to the cathode end of the x-ray tube.

Traditional packaging schemes for these miniature high voltage power supplies and x-ray tubes tend to use rigid boards with surface mounted components and a metal enclosure to contain the insulating material, minimize the emitted electrical noise and reduce the chance of corona which can lead to a degradation of the insulating material over time. Because of the proximity of the metal case to the high voltage components of the power supply, space between the components must be filled with materials that comprise a high dielectric breakdown strength. Traditional materials have included transformer oil, dielectric fluids, and polymeric potting materials. These materials usually have a high voltage breakdown strength of 400-800 volts/mil requiring a substantial thickness in order to insulate the high voltage (up to 60,000 volts). For example, a 500 volt/mil material would need a minimum of about 0.120" and normally a 100% safety margin is used resulting in a 0.240" requirement in all directions for electrical insulation.

In addition it is generally advantageous to position the x-ray devices within a portable XRF instrument in close proximity to the components that interact with a sample such as the components in the "nose" of a device that direct an x-ray beam to the sample. It is understood that x-ray radiation is a type of "ionizing" radiation that can be harmful to living tissue and thus it is generally appreciated that portable XRF devices are constructed to emit relatively low photon energies that typically attenuate over short distances (e.g. when an x-ray beam travels through air) in order to minimize the risk associated with operating an XRF device. Typically, the region of XRF devices near the nose of the instrument are very space constrained in the interest of making the XRF device easily manageable for a user and capable of fitting into small spaces where a sample resides. An example of an x-ray device constructed for use in a portable XRF instrument is described in U.S. Pat. No. 9,281,156, titled "Volumetrically Efficient Miniature X-Ray System", which is hereby incorporated by reference herein in its entirety for all purposes.

Therefore it is appreciated that there are significant advantages in having x-ray generators with high voltage multiplier components that comprise a dimension that fits into a region of a portable XRF device that is proximal to a sample to be tested while providing the necessary performance characteristics. For example, the desired solutions result in a versatile, low cost x-ray generator that provides laboratory grade performance in a portable XRF instrument.

SUMMARY OF THE INVENTION

An embodiment of a device for producing x-rays is described that comprises an x-ray tube and a high-voltage power supply electrically coupled to the x-ray tube, where the high-voltage power supply comprises a first stack of D shaped capacitors arranged in an opposed relationship with a second stack of D shaped capacitors.

The above embodiments and implementations are not necessarily inclusive or exclusive of each other and may be combined in any manner that is non-conflicting and otherwise possible, whether they are presented in association with a same, or a different, embodiment or implementation. The description of one embodiment or implementation is not intended to be limiting with respect to other embodiments and/or implementations. Also, any one or more function, step, operation, or technique described elsewhere in this specification may, in alternative implementations, be combined with any one or more function, step, operation, or technique described in the summary. Thus, the above embodiment and implementations are illustrative rather than limiting.

BRIEF DESCRIPTION OF THE DRAWINGS

The above and further features will be more clearly appreciated from the following detailed description when taken in conjunction with the accompanying drawings. In the drawings, like reference numerals indicate like structures, elements, or method steps and the leftmost digit of a reference numeral indicates the number of the figure in which the references element first appears (for example, element 120 appears first in FIG. 1). All of these conventions, however, are intended to be typical or illustrative, rather than limiting.

DETAILED DESCRIPTION OF THE INVENTION

Figure 1:
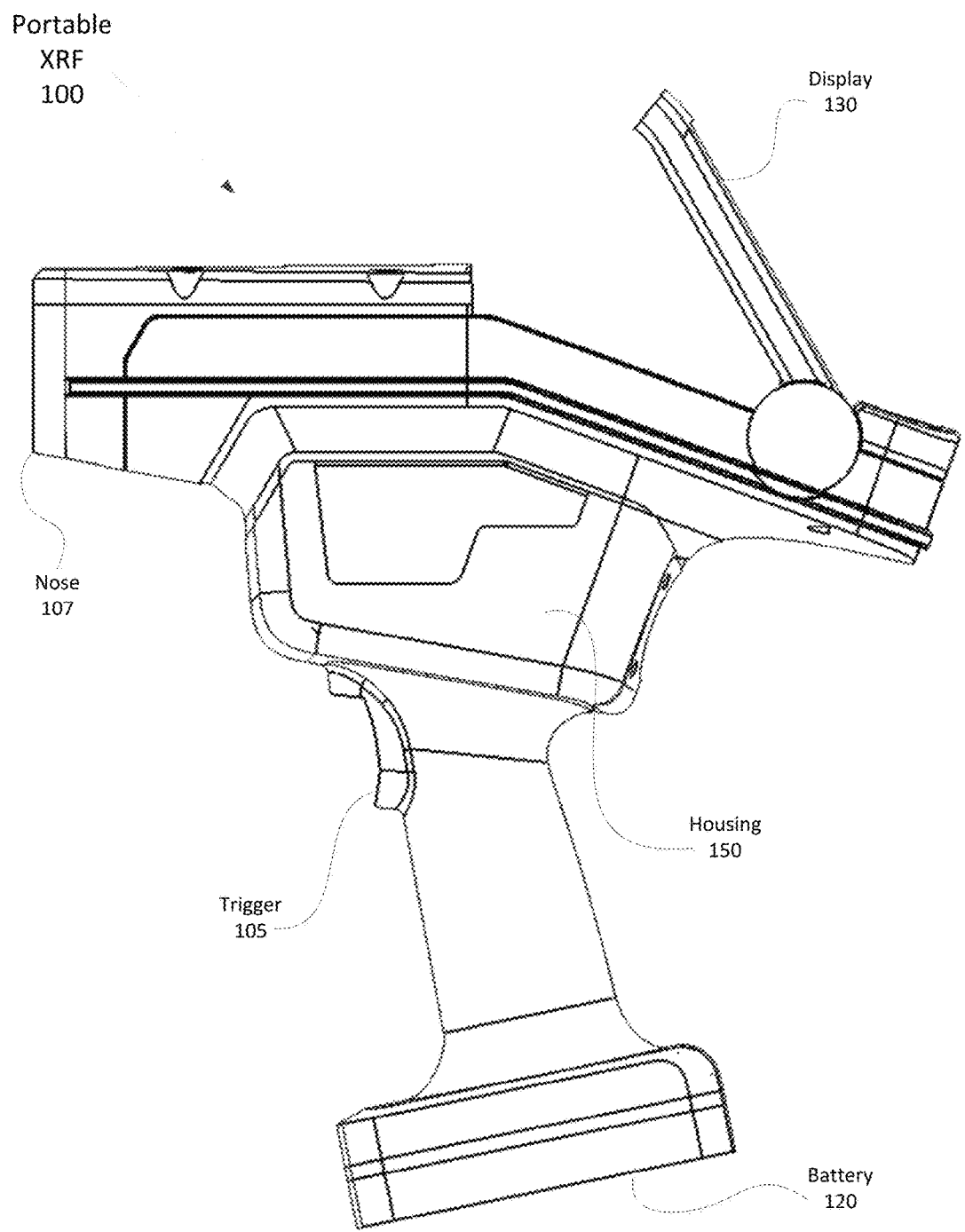
FIG. 1 is a simplified graphical representation of one embodiment of a portable XRF instrument.

Disclosed herein are methods and apparatus for providing a miniature high voltage multiplier incorporated into a small form x-ray source. In some embodiments the small form of the x-ray source is constructed to optimally fit into an internal space of a portable hand held XRF device in a desirable proximity for efficiently providing an x-ray beam to a sample.

Those of ordinary skill in the related art appreciate that it is highly desirable to construct a miniature high voltage multiplier with axially symmetric capacitors. However achieving the desired level of symmetry in a miniature form that includes sufficient capacitor size can be very difficult. In general the small form of the x-ray source includes novel circuit topology, component design, materials, and packaging. In order to provide some context, aspects of some of the terms used herein as well as a basic review of an x-ray source are now provided.

As discussed herein, the term "x-ray source" generally refers to a device used for generation of x-rays, and is not meant to imply a material for generation of x-rays, nor is it to be confused with prior art embodiments of x-ray generating equipment. Terms such as "small form," and "miniature" as well as "narrow form" and other similar terms used to characterize the high voltage multiplier, x-ray source, or other components should be considered as relative (such as with comparison to prior art technology), and taken to be descriptive of the nature of the embodiments disclosed herein. Such descriptive or relative terminology is not meant to imply a size standard or actual dimensions of the high voltage multiplier, x-ray source, or other component unless otherwise specified. Generally, the term "x-ray" refers to electromagnetic radiation having a wavelength in the range of about 0.01 nanometers (nm) to about 10 nm.

Those of ordinary skill in the art appreciate that many types of x-ray sources are well known. For example, typical x-ray source embodiments generally include control circuitry used to control at least one implementation of a high voltage transformer that outputs an AC voltage to a high voltage multiplier. The control circuitry also provides control over at least one implementation of a filament transformer and together with the high-voltage multiplier the combination drives an x-ray tube used to a generate x-ray beam.

Generally, the control circuit will receive inputs of desired operating voltage and current to maintain the operation of the x-ray source at desired output levels. In some embodiments, the operating voltage and current desired is defined by user input, such as through a user interface that may for instance include display 130 (e.g. a touch screen) or other computing device that may communicate with portable XRF 100 via WiFi, Bluetooth, USB cable, etc. For example, the control circuit may receive a 9V direct current (DC) input signal and generates a pulse-width modulated (PWM) 18 volt (V) peak-to-peak signal (alternating current, AC). The 18 V peak-to-peak signal is, in turn, supplied to the high voltage transformer that transforms the 18 VAC signal into a 0 to 5,000 volt peak-to-peak AC sine wave, based on the pulse width. The sine wave is fed into the high voltage multiplier that, in turn, multiplies the voltage to a level suited for driving the x-ray tube. For example, output of the high voltage multiplier may be a desired negative high voltage output (e.g. up to about 60,000 V). The DC high voltage output is applied to a cathode end of the x-ray tube. A potential difference between the cathode end of the x-ray tube, at negative high voltage, and the anode end of the x-ray tube (held at ground potential) serves as accelerating potential for electrons in the x-ray tube. The high voltage may be sensed by a feedback resistor so that the output can be accurately controlled to the desired operating voltage. Likewise, current may be sensed and used to control the pulse width applied to the filament transformer to control the beam current to the desired level. The high voltage is sensed by a very high resistance (e.g. 10 GOhm) resistor connected to the negative high voltage output. The current is sensed by a resistor connected to the diode at the bottom end of the multiplier, as the current entering the high voltage end of the multiplier is identical to the current leaving the low voltage end.

As described above, the described embodiments include a small form x-ray source configured to optimally fit into a spatially constrained location of a portable handheld device. More specifically the described embodiments include a miniature high voltage multiplier constructed to provide the necessary voltage output to effectively drive an x-ray tube (e.g. to produce an x-ray beam). For example, in portable applications it is highly desirable that a high voltage multiplier comprises an outside diameter (e.g. "OD") that is no larger than the OD of the x-ray tube used in portable applications, which in some embodiments may include an OD of about 0.56 inches. Also, in some embodiments the OD of a high voltage multiplier may be limited by the dimension of the diodes used in its construction.

Figure 2:
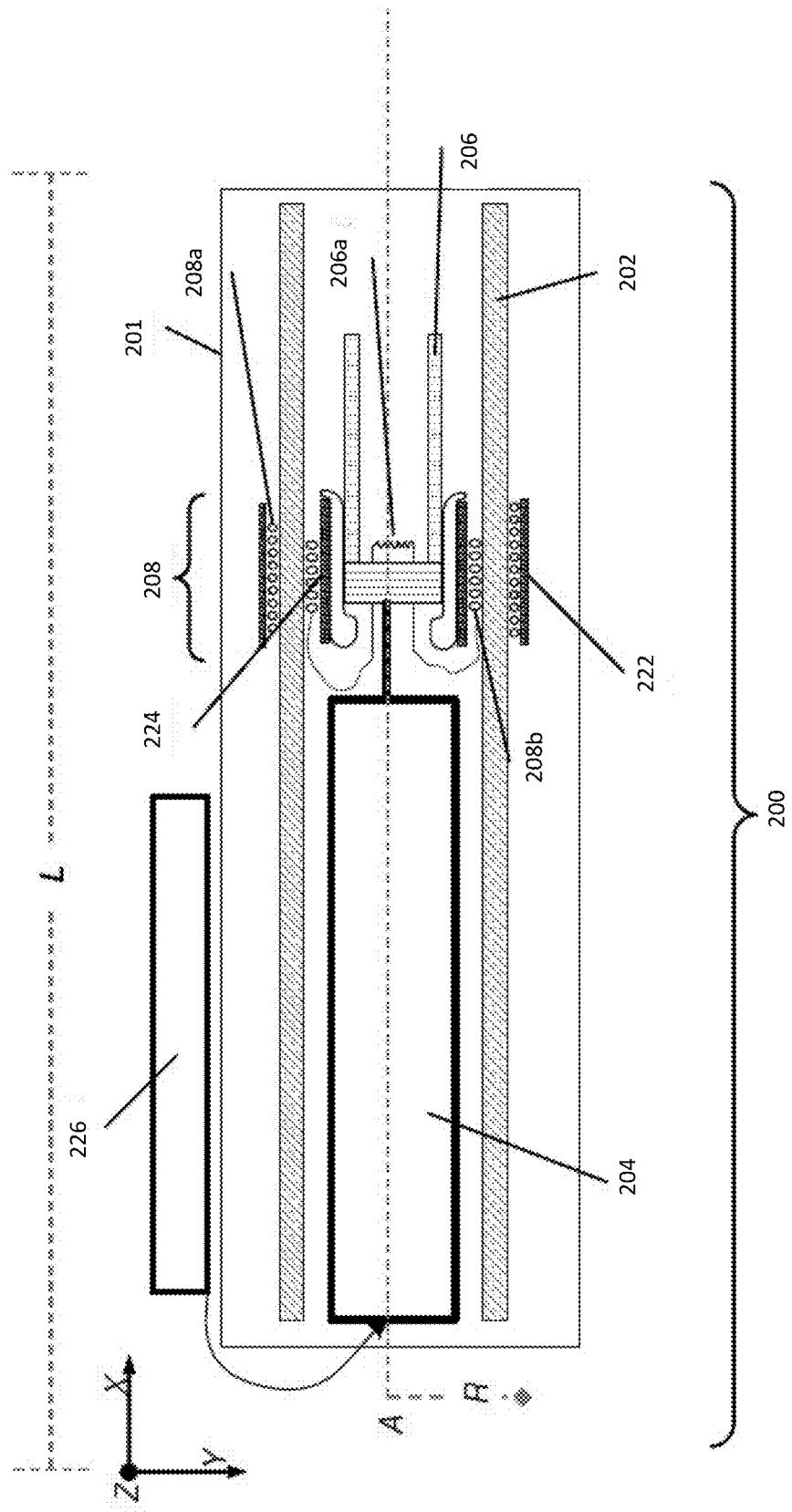
FIG. 2 is a simplified graphical representation of one embodiment of an x-ray source comprising a high voltage multiplier.

FIG. 1 provides an illustrative example of portable XRF 100 that includes trigger 105, nose 107, battery 120, display 130, and housing 150. Further FIG. 2 illustrates a cross-sectional view of an embodiment of x-ray source 200 according to the teachings herein. In this non-limiting example, x-ray source 200 is a generally cylindrical device, however the specific geometry of x-ray source 200 may be determined by a designer, manufacturer, or other similarly interested party. Such aspects may be selected, for example, in order to interface efficiently with a particular x-ray system, such as for example an embodiment of portable XRF 100. However for purposes of the discussion herein, it is considered that x-ray source 200 is a cylindrical device. In this embodiment, x-ray source 200 may be characterized as having a central axis, A, a length, L, and a radius, R.

In the embodiments described herein, x-ray source 200 is generally surrounded by insulating structure 202 that may comprise a tubular form. For example, insulating structure 202 may comprise an electrically insulating material, such as cross-linked polyethylene (PEX). Disposed within tubular insulating structure 202 is x-ray tube 206 (which includes an x-ray tube filament 206A) and high-voltage multiplier 204. In the described embodiments filament transformer 208 is disposed in both an external region and an internal region relative to insulating structure 202, as illustrated in FIG. 2 and described in U.S. Pat. No. 9,281,156, titled "Volumetrically Efficient Miniature X-Ray System", incorporated by reference above. However it will be appreciated that other embodiments may include filament transformer 208 positioned entirely in an external region relative to insulating structure 202.

In the embodiment represented in FIG. 2, insulating structure 202 is disposed in metallic housing 201 which can be designed to interface with external systems and devices. Disposed either in or on the metallic housing 201 is control circuit 226 coupled to high-voltage multiplier 204 and filament transformer 208. Filament transformer 108 includes an outer set of windings as primary coil 208A that is generally wrapped around the tubular housing 202. Filament transformer 208 also includes an inner set of windings as a secondary coil 208B that is generally wrapped around a base of a body for x-ray tube 206. In the described embodiment, x-ray tube 206 has a dimension such that, with secondary coil 208B wrapped thereabout, it will fit snugly within an inner diameter of tubular housing 202. Accordingly, the base of x-ray tube 206 (and therefore the secondary coil 208B) is aligned with primary coil 208A to provide for an effective transformer. The use of primary high voltage insulating structure 202 as the insulating material for filament transformer 208 eliminates a need for separate insulation for filament transformer 208 and allows the entire assembly to remain axially symmetric and compact.

An inner course magnetic material 224 and an outer course of magnetic 222 material is provided with the coils 208A, 208B. In some embodiments, magnetic material 224 and/or 222 includes a flexible magnetic material. Examples include various forms of magnetic foils, composite materials, ferrite cores, powdered metal cores, and other materials exhibiting similar properties. Suitable materials are commercially available from METGLAS of Conway, S.C. In some embodiments, magnetic materials 224 and/or 222 included in the filament transformer 208 are custom molded. In the described embodiments, magnetic material 224 and/or 222 concentrates the magnetic field in the windings of coils 208A and 208B, making filament transformer 208 more efficient and prevents the interior and exterior metallic components from acting like a shorted turn and reducing the electrical efficiency.

In some embodiments, control circuit 226 may be affixed to an interior or exterior of metallic housing 201 in any manner deemed appropriate. For example, control circuit 226 may be contained within a container, such as a nonconductive housing, and attached to metallic housing 201. In the same or alternative embodiments, a container for control circuit 226 may include appropriate shielding, such as shielding for electromagnetic interference (EMI) and/or radiation. Attaching control circuit 226 to metallic housing 201 may be performed in any manner deemed appropriate. For example, control circuit 226 (and any suitable mounting apparatus, such as a container or the like) may be glued, clipped, crimped, screwed, bonded, embedded or otherwise associated with metallic housing 201. Control circuit 226 may be at least partially disposed on the exterior of metallic housing 201. That is, at least a portion of control circuit 226 may also be disposed within the metallic housing 201. Accordingly, metallic housing 201 may include at least one penetration there through to provide for at least one of electrical connection and physical affixation of the control circuit 226.

Generally, metallic housing 201 is constructed of metal to provide for structural strength and radiation shielding as well as shielding from electromagnetic interference (EMI). Other metallic and/or structural materials may be used as deemed appropriate. The metallic structure of housing 201 may be adapted for fitting within another component such as an instrument making use of the x-ray source 200.

Filling of the void spaces within x-ray source 200 may be accomplished with a variety of different materials, such as what is typically referred to as "potting" material or compound. Those of ordinary skill in the related art appreciate that the term "potting" generally refers to filling an electronic assembly with a compound that excludes moisture and corrosive agents and that provides resistance to shock and vibration. Potting compounds may include, but are not limited to polybutadiene formulations, silicone-based elastomer formulations, a fluid dielectric such as transformer oil or a fluorinated hydrocarbon, perfluorinated fluids, and suitable high voltage insulating gas such as sulfur hexafluoride.

In some embodiments, use of a fluid or gas potting material is advantageous to provide access to the electronics contained within x-ray source 200. For example, a fluid or gas insulating material enables component removal such as high-voltage multiplier 204 and/or filament transformer 208. Removal of components may be advantageous or desired for maintenance and other similar purposes. In the present example, the potting material may include sulfur hexafluoride gas, or dielectric fluid.

Also, in some embodiments additional shielding materials may be added to the potting material to help shield stray X radiation from penetrating x-ray tube 206. For example, non-conducting oxides of at least one of lead, tungsten, and bismuth may be added to polymeric potting material to help reduce stray radiation coming from the x-ray source 200.

Generally, control circuit 226, high-voltage multiplier 204, x-ray tube 206, and filament transformer 208 are electrically connected with appropriate electrical connections. The electrical connections may include wires, vias, clips, mounts, and other types of connections and connecting components. Void space within x-ray source 200 must be displaced by insulating material such as a potting material as described above. In typical embodiments, the potting material chosen provides adequate electrical isolation along the axis, A, as well as enhancement of structural integrity of the physical arrangement of the various components within x-ray source 200.

In the described embodiments, the high-voltage multiplier 204 may be constructed as a "Cockcroft Walton" type of high-voltage multiplier. Those of ordinary skill in the art understand that embodiments of a "Cockcroft Walton" type of voltage multiplier converts AC or pulsing DC electrical power from a low voltage level to a higher DC voltage level. This includes a ladder network comprising "stages" of capacitors and diodes to generate high voltages. Using only capacitors and diodes, the high-voltage multiplier may be configured to step-up relatively low voltages to extremely high values, while at the same time being far lighter and cheaper than designs that make use of transformers. Advantageously, the voltage across each stage of the ladder network is equal to only twice the peak input voltage in a half wave rectifier. Further, this has the advantage of enabling use of relatively low cost components and being easy to insulate.

As a matter of convention, it may be considered that a base of x-ray source 200 is a "near" side, while an open end of x-ray source 200 may be referred to as a "far side."

Figure 3A:
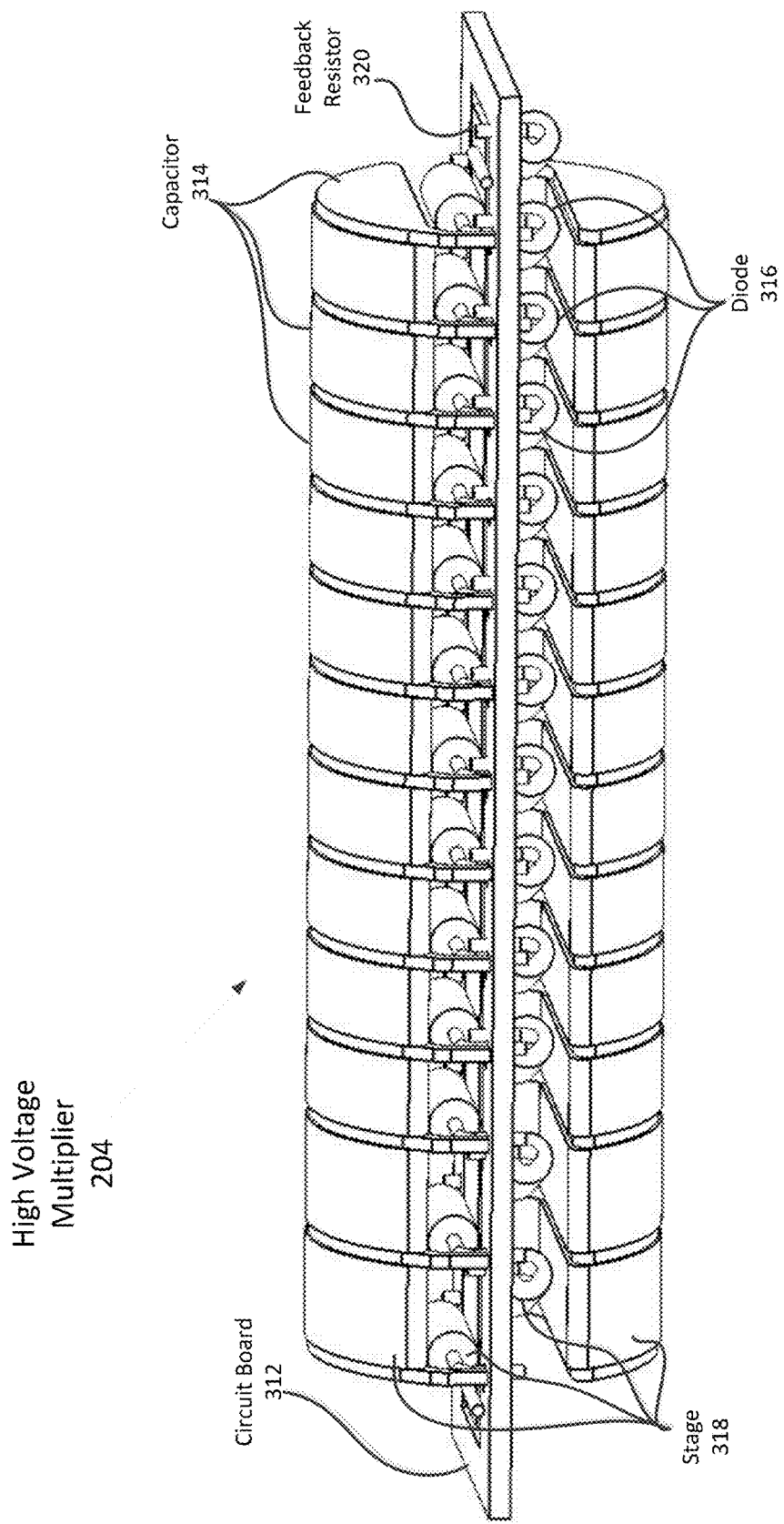
FIG. 3A is a simplified graphical representation of a side view of one embodiment of the high voltage multiplier of FIG. 2.
Figure 3B:
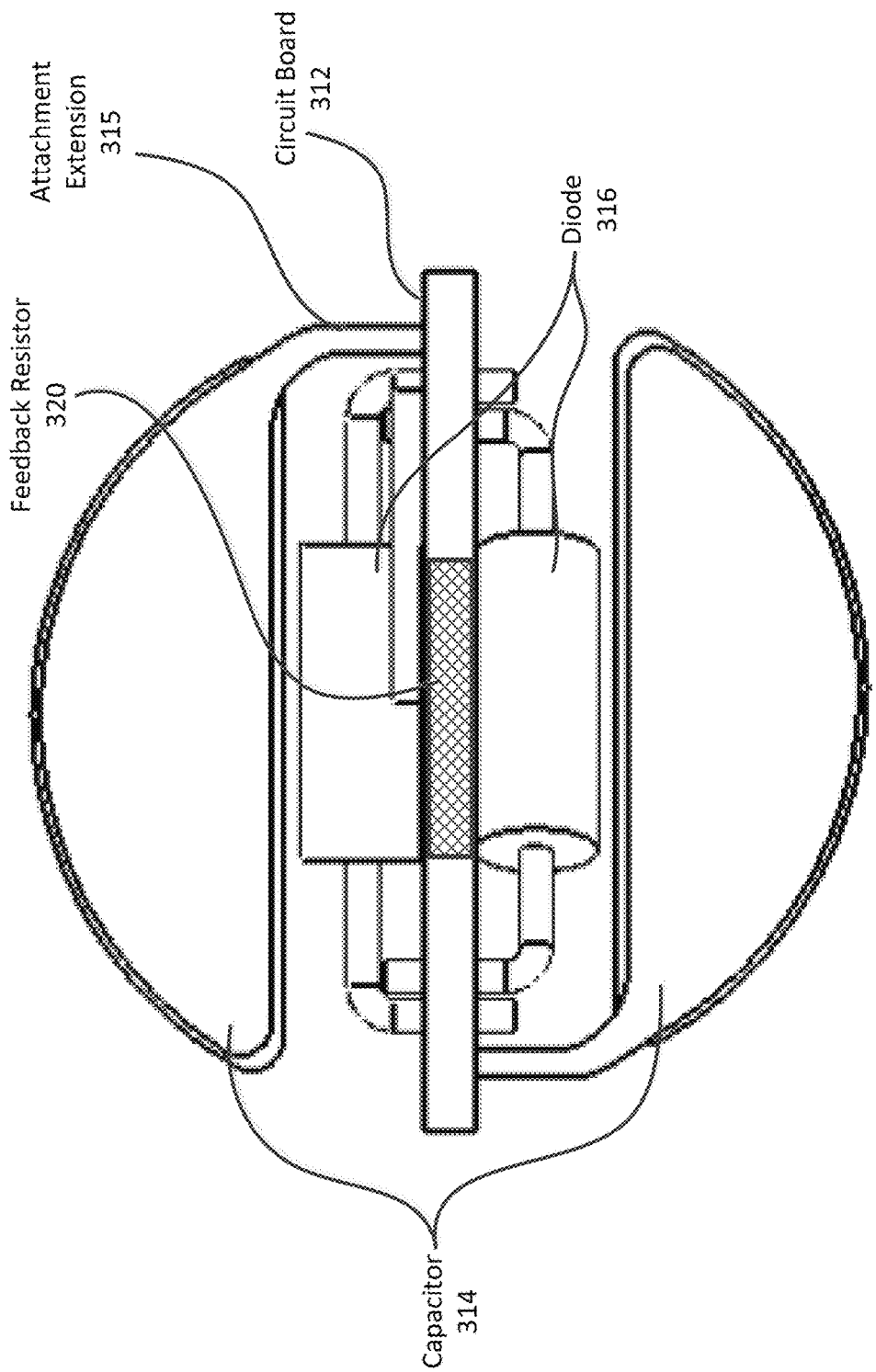
FIG. 3B is a simplified graphical representation of an end view of one embodiment of the high voltage multiplier of FIG. 2.

FIGS. 3A and 3B provide illustrative examples of high voltage multiplier 204 that includes a plurality of capacitors 314, and a plurality of diodes 316 disposed on circuit board 312. In the described embodiments, each of capacitors 314 comprises a "D" shape that provides significant advantages for use in a miniature cylindrical format such as by providing a large enough capacitance that allows for a highly desirable alignment of the voltage gradient across capacitors 314, diodes 316, and feedback resistor 320 of high voltage multiplier 204. For example, the "D" shape of capacitors 314 provides an advantageous degree of volume when used in cylindrical applications which increases the amount of capacitance relative to other configurations. Additionally, the "D" shape of capacitors 314 are more mechanically robust (e.g. more resistant to mechanical insult) than other miniature capacitor embodiments and are more easily manufactured.

Capacitors 314 may also be constructed from various materials having different dielectric constant values and may exhibit different characteristics depending upon specific configuration of x-ray source 200, application, and environmental factors. For example, there may be tradeoffs associated with dielectric materials where some materials with a high dielectric constant may compromise with respect to its temperature coefficient and be less electrically/mechanically stable relative to other materials with low dielectric constant. In some cases, certain limitations of materials may be addressed with other components such as, for instance, using an embodiment of primary hv transformer that runs at a high frequency (e.g. 80-100 KHz) however there may be other tradeoffs with these approaches as well (e.g. size of transformer required). In the present example, one type of material having desirable dielectric constant characteristics may include a ceramic material.

Further, each of capacitors 314 uses a "cantilever" approach for attachment to circuit board 312 that isolates vibration and utilizes space efficiently. For example, as illustrated in FIGS. 3A and 3B each of capacitors 314 are substantially planar and include a straight edge and a semicircular edge. Also, at one point where the straight edge meets the semi-circular edge, each of capacitors 314 comprises attachment extension 315 configured for coupling to circuit board 312 using techniques known to those of ordinary skill in the related art (e.g. soldering, etc.).

Also, in the same or alternative embodiments, diodes 316 may comprise desirable characteristics that include a small dimension that enables the construction of the overall miniature form of high voltage multiplier 204, as well as fast recovery times of about 20 ns and low capacitance value of about 0.3 pF. For example, as illustrated in FIGS. 3A and 3B the dimension of diodes 316 enable the arrangement of components in high voltage multiplier 204 such that diodes 316 are positioned between capacitors 314 and circuit board 312 (e.g. on both sides of circuit board 312) which provides a compact form desirable for a miniature cylindrical arrangement.

Also, as described above diodes 316 should have the smallest possible dimension for the miniature high voltage multiplier embodiments described herein. For example, as illustrated in FIGS. 3A and 3B diodes 316 may include a cylindrical form that may be about 2 mm in diameter, although it will be appreciated that diodes 316 can be smaller or larger depending upon available technology and dimension limitations associated with high voltage multiplier 204.

Collectively, capacitors 314 are electrically coupled with diodes 316 to provide for high-voltage multiplier 204. For example, high-voltage multiplier 204 includes a plurality of stages 318 each comprising a pair of capacitors 314 (e.g. capacitors 314 arranged in an opposed relationship) and a respective pair of high-voltage diodes 316. As is known in the art of Cockcroft Walton types of voltage multipliers, each of the respective stages 318 mimics components and construction of the first stage, and generally provides for a stepping of the input voltage.

Embodiments of high voltage multiplier 204 comprise 12-14 implementations of stages 318, although there is no restriction on the number of stages 318 used. However, as the number of stages 318 increases (e.g. >15 stages) the hv transformer may be required to provide more voltage.

The embodiments of high voltage multiplier 204 illustrated in FIGS. 3A and 3B are arranged as a stack of single layer capacitors which provides an advantage in the manufacture of high voltage multiplier 204 due to the relative ease of mounting capacitors 314 as compared to a multi layer capacitor arrangement. It will, however, be appreciated that capacitors 314 of high voltage multiplier 204 could also be arranged in a multi layer capacitor arrangement. For example, the single layer format of capacitors 314 can be pre-assembled as a stack that can then be operatively connected to circuit board 312. Further, the single layer capacitor arrangement has a significantly larger breakdown voltage per cap (e.g. a voltage value at which a capacitor becomes irreversibly conductive) and better efficiency than multi layer capacitor arrangements that provides an advantage in high voltage multiplier embodiments. For example, the single layer capacitor arrangement may comprise a breakdown voltage value of about 25 kV versus a breakdown voltage value of about 9-10 kV seen with multi layer capacitor arrangements.

Included within high-voltage multiplier 204 is at least one embodiment of feedback resistor 320 as illustrated in FIGS. 3A and 3B. For example, feedback resistor 320 may include a precision high-voltage resistor that comprises about the same length as high-voltage multiplier 204 to reduce the voltage gradient (also sometimes referred to as a "potential gradient") between adjacent capacitor/diode stages of the high-voltage multiplier 204 and the resistor 320, thus reducing leakage currents and enhancing the accuracy of the high voltage measurement. Also, in the present example illustrated in FIGS. 3A and 3B, feedback resistor 320 is positionally located in a slot of circuit board 312 so that it is in the same plane as board 312 which improves the miniature form of high voltage multiplier 204.

Also in the same or alternative embodiments, one or more additional surge resistors may be operatively coupled to circuit board 312 between the stacks of capacitors 314 and a contact element associated with high voltage multiplier 204 that electrically couples high voltage multiplier 204 with x-ray tube 206. In some embodiments the contact element may include a spring (e.g. constructed of electrically conductive material) or other type of contact element that maintains the electrical coupling under conditions that include shock or vibration.

In the embodiments described herein circuit board 312 may employ a variety of different technologies that includes flexible printed circuit boards (PCB), rigid printed circuit boards (such as those having traditional layouts), a sectioned printed circuit board (such as one outfitted with flexible hinges, ribbon cables, or the like), a rigidized circuit board (such as one with flexible sections), circuit boards including rigid sections with pin connectors and or wires may be used as well. Various other physical or mechanical modifications of the circuit board 112 may be incorporated.

As described herein, embodiments of portable XRF 100 utilize x-ray source 200 to generate an x-ray beam. For example, portable XRF 100 comprises housing 150 with an internal space constructed to position x-ray source 200 in close proximity to nose 107 that comprises a window. Housing 150 is further constructed to position at least one detector 314 in optical communication with the window. In the presently described example, the window may include a thin sheet of x-ray transparent material, such as a polyimide film (e.g. the polyimide film may include KAPTON from E.I. duPont deNemours and Company of Wilmington Del.), to prevent dirt or other contaminants from entering through nose 107. In operation, x-ray source 200 produces an x-ray beam that is directed through the window to irradiate a sample that fluoresces in response to the x-ray beam. At least a portion of the fluorescence emission from the sample passes back through the window and is detected by the detector(s) that communicates with a processor to provide a spectral analysis of the sample.

X-ray source 200 may be used for any device that requires or makes use of relatively low power x-ray tubes. For example x-ray source 200 may be used with smaller x-ray diffraction or x-ray imaging systems. Advantageously, by making use of the smaller form of x-ray source 200, portable XRF 100 may also be provided in a smaller form. Additionally, in some embodiments, by using the smaller form of x-ray source 200, manufacturers may dispense with use of radioactive sources. By offering a device that does not include radioactive sources, manufacturers are able to more freely and cheaply offer and distribute their respective devices.

The tubular insulating structure 202 may be fabricated from a variety of materials. Suitable materials for the tubular insulating structure 202 generally include materials that exhibit high dielectric strength (such as on the order of 2000 V/mil to 7000 V/mil. Ultrahigh molecular weight or cross-linked polyethylene (PEX) material (exhibiting a dielectric of about 2300 V/mil) may be used. Other suitable materials include KAPTON and MYLAR, as well as fused silica and quartz.

Although the housing has been disclosed as a metallic housing 101 that includes a tubular insulating structure 202, which may be considered to be generally circular, this is not a requirement. Extrusions of other cross-sectional geometries may be used (e.g., hexagonal, rectangular, etc.).

An exemplary embodiment of the x-ray tube 206 is described in U.S. Pat. No. 7,657,003, issued Feb. 2, 2010, and entitled "x-ray tube with enhanced small spot cathode and methods for manufacture thereof", which is hereby incorporated by reference herein in its entirety for all purposes. For example, the '003 patent discloses an x-ray source that produces a well-defined electron beam, without an undesirable halo. The x-ray source includes a housing, a cathode disposed within the housing, an anode spaced apart from the cathode for accelerating electrons emitted from the cathode and an x-ray emitter target disposed within the housing and spaced apart from the cathode for impact by the accelerated electrons. The cathode, by virtue of the fact that the emission area is planar and that it is surrounded by a metallic non-emitting area that is coplanar, emits electrons that are easily focused into a small spot by the remaining elements of the tube, without spurious electron trajectories that create the undesirable halo. This patent is incorporated by reference herein in its entirety, with the exception that if any subject matter therein is in conflict with the present disclosure, then the subject matter of the present disclosure shall prevail.

As a result, the teachings herein provide for an x-ray source of a drastically reduced size. While the x-ray source has a substantially reduced volume, it also has a substantially reduced cost, an improved assembly process, a reduced weight and a reasonable output. It is also possible to manufacture without using irreversibly curing potting materials, which allows repair of malfunctioning components. This greatly increases manufacturing yield and reduces the cost of repairing failures in the field.

Having described various embodiments and implementations, it should be apparent to those skilled in the relevant art that the foregoing is illustrative only and not limiting, having been presented by way of example only. Many other schemes for distributing functions among the various functional elements of the illustrated embodiments are possible. The functions of any element may be carried out in various ways in alternative embodiment.

What is claimed is:

1. A device for producing x-rays, the device comprising:
an x-ray tube; and
a high-voltage power supply electrically coupled to the x-ray tube, wherein the high-voltage power supply comprises a first stack of D shaped capacitors arranged in an opposed relationship with a second stack of D shaped capacitors, wherein each D shaped capacitor is substantially planar and comprises a straight edge and a semi-circular edge.

2. The device of claim 1, wherein:
the first and second stacks each comprise a single layer capacitor arrangement comprising a breakdown voltage value of about 25kV.

3. The device of claim 1, wherein:
the first stack of D shaped capacitors is separated from the second stack of D shaped capacitors by a circuit board.

4. The device of claim 3, wherein:
the first and second stacks attach to the circuit board in a cantilevered arrangement.

5. The device of claim 3, wherein:
the D shaped capacitors comprise an attachment extension that attaches to the circuit board.

6. The device of claim 3, further comprising:
a feedback resistor positioned in the same plane as the circuit board.

7. The device of claim 6, further comprising:
the feedback resistor is positioned in a slot of circuit board.

8. The device of claim 1, further comprising:
a plurality of diodes positioned between the first and second stacks of D shaped capacitors.

9. The device of claim 8, further comprising:
the diodes comprise a cylindrical form of about 2 mm in diameter.

10. The device of claim 8, further comprising:
the diodes comprise a fast recovery time of about 20 ns and a low capacitance value of about 0.3 pF.

11. The device of claim 1, wherein:
the straight edge of the first stack of D shaped capacitors is opposed to the straight edge of the second stack of D shaped capacitors.

12. The device of claim 1, wherein:
the first and second stacks comprises a network of stages.

13. The device of claim 12, wherein:
the network of stages comprises 12 stages.

14. The device of claim 12, wherein:
each stage comprises a D shaped capacitor from the first stack and a D shaped capacitor from the second stack.

15. The device of claim 1, further comprising:
a contact element that electrically couples the high-voltage power supply with the x-ray tube.

16. The device of claim 15, wherein:
the contact element comprises a spring.

17. The device of claim 1, wherein:
the high-voltage power supply comprises an outside diameter of about 0.56 inches.

* * * * *